United States Patent [19]
Elftman

[11] Patent Number: 5,120,313
[45] Date of Patent: * Jun. 9, 1992

[54] METHOD FOR MEASUING BLOOD PRESURE IN AN ANIMAL OR HUMAN USING A PERCUTUANEOUS ACCESS PORT

[75] Inventor: Nancy W. Elftman, 1020 Nashport, La Verne, Calif. 91750

[73] Assignee: Nancy W. Elftman, La Verne, Calif.

[*] Notice: The portion of the term of this patent subsequent to Dec. 13, 2005 has been disclaimed.

[21] Appl. No.: 749,755

[22] Filed: Mar. 20, 1990

Related U.S. Application Data

[63] Continuation of Ser. No. 283,185, Dec. 12, 1988, abandoned, which is a continuation of Ser. No. 845,574, Mar. 28, 1986, Pat. No. 4,790,826.

[51] Int. Cl.$^5$ .............................................. A61M 5/32
[52] U.S. Cl. .................................... 604/175; 128/673; 128/748
[58] Field of Search .................... 604/51, 52, 174, 175, 604/891.1; 128/637, 645, 672, 673, 692, 675, 748

[56] References Cited

U.S. PATENT DOCUMENTS

| | | | |
|---|---|---|---|
| 2,976,865 | 3/1961 | Shipley | 128/675 |
| 3,466,742 | 9/1969 | Sinclair | 128/692 |
| 3,466,742 | 9/1969 | Sinclair | 128/692 |
| 3,565,056 | 2/1971 | Statham | 128/748 |
| 3,610,228 | 10/1971 | Temkin | 128/748 |
| 3,663,965 | 5/1972 | Lee, Jr. et al. | |
| 3,783,868 | 1/1974 | Bokros | |
| 3,826,257 | 7/1974 | Buselmeier | |

(List continued on next page.)

OTHER PUBLICATIONS

Butterfield, J. and Decker, G., "A Simple Device for Exteriorizing Chronically Implanted Catheters in Dogs" *Laboratory Animal Science*, vol. 34, No. 2 (Apr., 1984), pp. 206–208.

Implantable Pressure Transducers for Animal Research from Konigsberg Instruments, Inc., Pasadena, Calif., 91107, Jun. 1, 1982.

Transducer Implantion, author Kenneth J. Dormer, *Medical Electronics*, Oct. 1980 pp. 69–75.

Norfolk Medical Products, Inc. "Vascular-Access-Port Model SLA," Skokie, Ill. 60076-No Date.

*Primary Examiner*—Stephen C. Pellegrino
*Assistant Examiner*—Ralph A. Lewis
*Attorney, Agent, or Firm*—Dunlap, Codding & Lee

[57] ABSTRACT

A percutaneous access port for providing access to a selected organ in an animal which includes a base assembly and a septum assembly. The base assembly has a fluid chamber formed in a portion thereof generally between an upper and a lower end of the base assembly with an inlet port being formed in a portion in the base assembly gnerally near the lower end of the base assembly. The inlet port is adapted to be connected to the selected organ to provide communication between the fluid chamber in the base assembly and the selected organ. At least one access port is formed through the upper end of the base assembly with each access port extending a distance through the base assembly and intersecting the fluid chamber to provide communication between the upper end of the base assembly and the fluid chamber. The septum assembly includes a portion which extends across each access port in the base assembly to resealably seal each access port, each access port providing resealable access to the fluid chamber. A transducer is disposed in the fluid chamber of the base assembly and the transducer is adapted to detect the pressure of the fluid within the fluid chamber and to provide an output transducer signal indicative of the pressure of the fluid in the fluid chamber, the transducer providing output signal continuously providing an output indication of fluid pressure in an implanted condition of the base assembly with the transducer connected thereto.

2 Claims, 2 Drawing Sheets

U.S. PATENT DOCUMENTS

| | | | |
|---|---|---|---|
| 4,015,601 | 4/1977 | Bokros et al. | |
| 4,092,983 | 6/1978 | Slivenko | |
| 4,108,173 | 8/1978 | Slivenko et al. | |
| 4,108,174 | 8/1978 | Slivenko | |
| 4,210,029 | 7/1980 | Porter | 128/673 |
| 4,318,401 | 3/1982 | Zimmerman | |
| 4,344,435 | 8/1982 | Aubin | |
| 4,393,873 | 7/1983 | Nawash et al. | |
| 4,403,615 | 9/1983 | Hoehner | 128/692 |
| 4,407,296 | 10/1983 | Anderson | 128/675 |
| 4,581,020 | 4/1986 | Mittleman | 604/175 |
| 4,585,010 | 4/1986 | Ascer et al. | 128/673 |
| 4,600,013 | 7/1986 | Landy et al. | 128/748 |
| 4,628,928 | 12/1986 | Lowell | 128/673 |
| 4,646,752 | 3/1987 | Swann et al. | 128/748 |
| 4,654,033 | 3/1987 | Lapeyre et al. | 604/175 |
| 4,705,499 | 11/1987 | Hooven | 128/748 |
| 4,733,652 | 3/1988 | Kantrowitz | 128/672 |
| 4,790,826 | 12/1988 | Elftman | 604/175 |
| 4,796,641 | 1/1989 | Mills et al. | 128/748 |

METHOD FOR MEASURING BLOOD PRESURE IN AN ANIMAL OR HUMAN USING A

CROSS REFERENCE TO RELATED APPLICATIONS

This is a continuation of co-pending application Ser. No. 283,185 filed on Dec. 12, 1988 now abandoned which is a continuation of co-pending application Ser. No. 845,574 filed on Mar. 28, 1986 now U.S. Pat. No. 4,790,826. Related subject matter is disclosed in U.S. patent application Ser. No. 283,251, filed Dec. 12, 1988, now abandoned entitled Method for Using Percutaneous Access Port.

FIELD OF THE INVENTION

The present invention relates generally to percutaneous access ports and, more particularly, but not by way of limitation, to a percutaneous access port having access ports which communicate with a fluid chamber and a transducer disposed in the fluid chamber for detecting the pressure of the fluid in the fluid chamber.

SUMMARY OF THE INVENTION

A device adapted to be percutaneously implanted in a human, rat or other animal to provide continuous access to a body organ through fluid communication. During implantation, the percutaneous access port 10 is connected to a selected body organ or cavity so that the fluid chamber 14 of the device is in fluid communication with that organ or cavity. An upper end portion of the device extends through the skin and comprises at least two access ports in communication with the fluid chamber. Resealable access to the fluid chamber through the access ports is provided by a septum assembly. In a preferred embodiment, a transducer is disposed within the fluid chamber for detecting the pressure of the fluid.

BRIEF DESCRIPTION OF THE PREFERRED EMBODIMENTS

Figure 1:
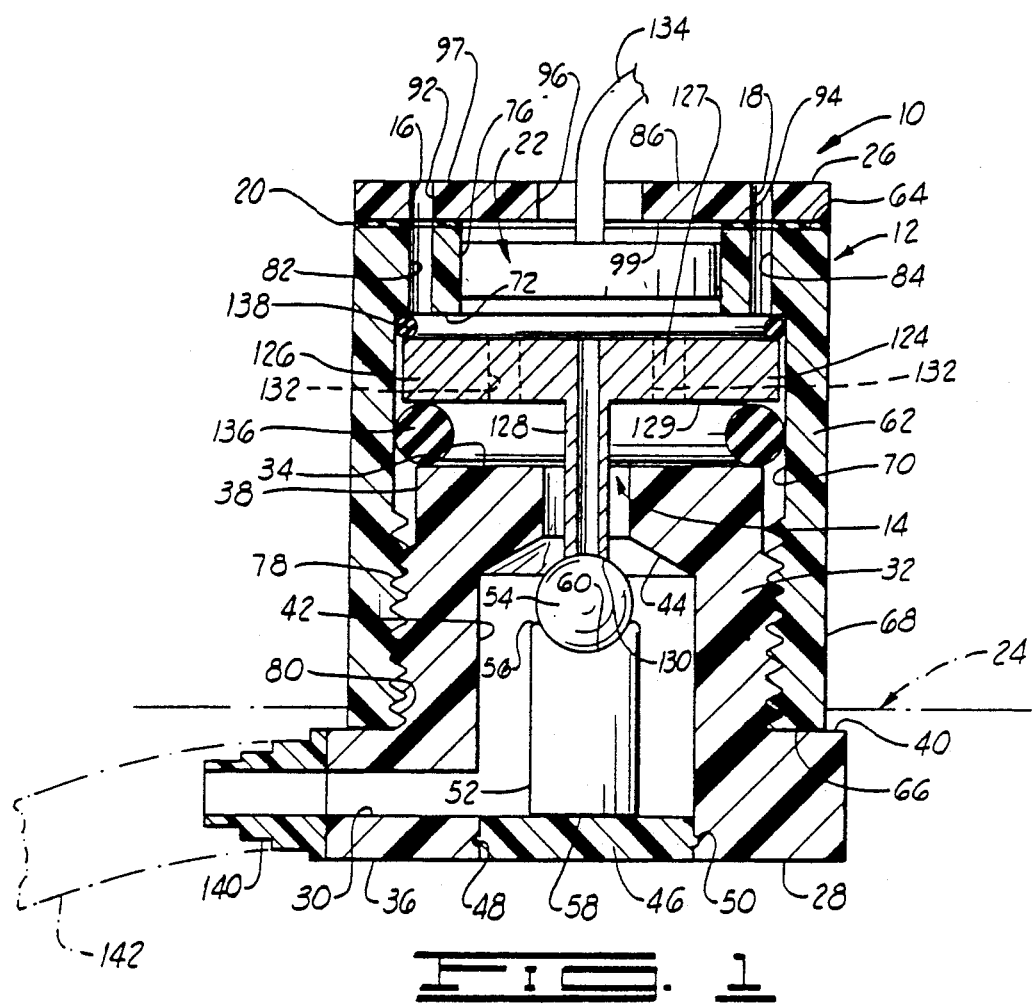
FIG. 1 is a sectional view of a percutaneous access port which is constructed in accordance with the present invention.
Figure 2:
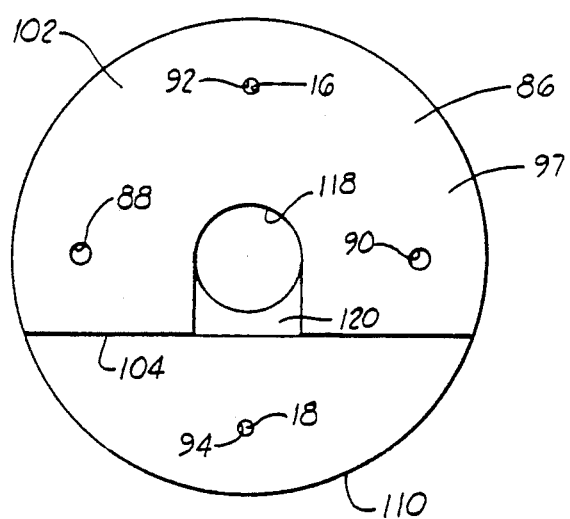
FIG. 2 is a top view of the percutaneous access port of FIG. 1.
Figure 3:
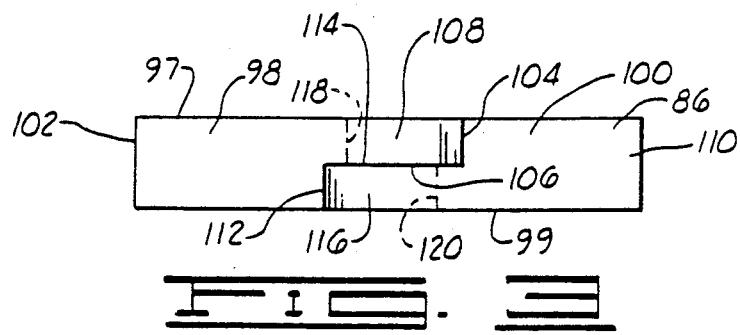
FIG. 3 is a sectional view of the cap portion of the base assembly shown in FIG. 1, the top of the cap being shown in FIG. 2.

Referring to FIGS. 1, 2, and 3, shown therein and designated by the general reference numeral 10 is a percutaneous access port which is constructed in accordance with the present invention. In general, the percutaneous access port includes a base assembly 12 having a fluid chamber 14 formed in a portion thereof and having a plurality of access ports formed through a portion thereof in fluidic communication with the fluid chamber 14, two access ports being shown in FIGS. 1 and 2 and designated therein by the reference numerals 16 and 18. A septum assembly 20 is connected to the base assembly 12 and a portion of the septum assembly 20 extends across each access port 16 and 18 for sealing each access port 16 and 18, the septum assembly 20 being adapted to provide resealable access through the septum assembly 20 to the fluid chamber via either one or both of the access ports 16 and 18. A transducer assembly 22 is disposed in the base assembly 12 and a portion of the transducer assembly 22 is in communication with the fluid chamber 14. The transducer assembly 22 is adapted to sense or detect the pressure of the fluid in the fluid chamber 14 and to provide an output transducer signal indicative of the pressure of the fluid within the fluid chamber 14.

The percutaneous access port 10 is adapted to be implanted in an animal such as a human or rat or cow other such animal. During implantation, the percutaneous access port 10 is connected to a selected organ (internal body part) in the warm blooded animal so that the fluid chamber 14 is in communication with the selected organ in the warm or cold blooded animal and an upper end portion of the percutaneous access port 10 extends through the outer layer of skin of the animal so the upper end portion of the percutaneous access port 10 is disposed above the outer layer of skin in an implanted condition of the percutaneous access port 10, the upper layer of skin being diagrammatically shown in FIG. 1 and designated therein by the reference numeral 24. Thus, in the implanted condition of the percutaneous access port 10, an upper end portion of the base assembly 12 extends through and above the outer layer of skin 24 thereby providing continuous access to the selected organ in the animal by way of either one or both of the access ports 16 which are in fluidic communication with the selected organ by way of the fluid chamber and the connection of the fluid chamber to the selected organ and providing a continuous transducer output signal indicative of the pressure of the fluid within the fluid chamber 14. The percutaneous access port 10 of the present invention provides quick, safe and accurate measurement of fluid pressure, particularly blood pressure, in conscious animals and is useful in relatively small animals down to a size of a three hundred gram rat. In an implanted condition of the percutaneous access port, the transducer assembly 22 provides continuous transducer output signals indicative of the pressure of the blood or fluid in the fluid chamber 14 and, at the same time, the access ports 16 and 18 provide access to the fluid chamber 14 for flushing the fluid chamber 14 or for infusion of substances into the fluid within the fluid chamber.

It particularly should be noted that the percutaneous access port 10 of the present invention provides a means for measuring vascular pressures in small, conscious animals down to the size of a three hundred gram rat, as mentioned before. Large animals such as dogs and cats are becoming relatively expensive and there is growing pressure to prevent medical research from utilizing large animals such as dogs and cats. Thus, it is becoming extremely important to be able to utilize relatively smaller animals for research, and the percutaneous access port 10 of the present invention provides a small, implantable device for quickly, safely and accurately measuring blood pressure in conscious animals in a manner which reduces time and maintenance during the performance of experiments on large numbers of such animals. In addition, the percutaneous access port 10 can be utilized to provide chronic infusion ports for pharmacological studies, chronic sampling from vessels, direct access to any organ cavity (intrauterine access for artificial insemination of cattle), for example, and other applications as will be apparent to those skilled in the art from the following detailed description.

The base assembly 12, more particularly, has an upper end 26 and a lower end 28 and the fluid chamber 14 is formed in the base assembly 12, generally between the upper and the lower ends 26 and 28. An inlet port 30 is formed in a portion of the base assembly 12, generally near the lower end 28 thereof. The inlet port 30 is connectable to the selected organ by catheter, for example, and the inlet port 30 is in communication with the fluid chamber 14 thereby providing communication between the fluid chamber 14 and the selected organ. The access ports 16 and 18, more particularly, extend through the upper end 26 of the base assembly 12 and each of the access ports 16 and 18 extends a distance through the base assembly 12 intersecting the fluid chamber 14 to provide communication between the upper end 26 of the base assembly 12 and the fluid chamber 14. The inlet port 30 is formed through a lower end portion 28 of the base assembly 12 and the inlet port 30 extends a distance through the base assembly 12 intersecting the fluid chamber 14, the inlet port 30 being located below the upper skin 24 level in an implanted condition of the percutaneous access port 10.

The base assembly 12 more particularly, includes a lower base 32 having an upper end 34, a lower end 36 and an outer peripheral surface 38. A flange 40 is formed on the outer peripheral surface 38 generally adjacent to the lower end 36 of the lower base 32 and the flange 40 extends a distance radially from the outer peripheral surface 38 of the lower base 32. An opening 42 extends through the upper end 34 of the lower base 32 and the opening 42 extends a distance through the lower base 32 generally between the upper and the lower ends 34 and 36, the opening 42 intersecting the lower end 36 of the lower base 32, in one embodiment as shown in FIG. 1.

The inlet port 30, more particularly, extends through the outer peripheral surface of the flange 40 and through the flange 40 and through the lower base 32 and intersects the opening 42 and the lower base 32. A portion of the opening 42 generally at the upper end 34 of the lower base 32 has a smaller diameter as compared to the remaining portion of the opening 42, thereby forming a sealing surface 44 in the lower base 32. The sealing surface 44 is positioned generally between the upper and the lower ends 34 and 36 of the lower base 32 and the sealing surface 44 extends circumferentially about the opening 42 in the lower base 32.

The lower base 32 also includes a circularly shaped disc 46. A recess 48 is formed in the wall of the lower base formed by the opening 42 and the recess 48 is positioned generally near the lower end 36 of the lower base 32. A ring 50 is formed on the outer peripheral surface of the disc 46 and the disc 46 is sized and shaped to fit into the opening 42 in the lower base 32 to a position wherein the ring 50 snaps into the recess 48 thereby securing the disc 46 in the lower base 32. The disc closes the opening 42 at the lower end 36 of the lower base 32.

The percutaneous access port 10 also includes a spring 52 and a seal member 54. The spring 52 preferably is cylindrically shaped and is constructed of a silicone rubber material. The spring 52 has an upper end 56 and a lower end 58 and a circularly shaped recess 60 is formed in the upper end 56 of the spring 52. The seal member 54 is spherically shaped and is constructed preferably of stainless steel.

In an assembled position, the spring 52 is positioned in the opening 42 of the lower base 32 with the lower end 58 of the spring 52 being supported on the disc 48 portion of the lower base 32. The seal member 54 is positioned in the recess 60 in the upper end 56 of the seal member 54. The seal member 54 and the spring 52 each are sized and shaped so that the spring 52 biases the seal member 54 into sealing engagement with the sealing surface 44 formed in the lower base 32, the seal member 54 cooperating with the sealing surface 44 to sealingly close the opening 42 in the lower base 32 when the seal member 54 sealingly engages the sealing surface 44 in the lower base 32.

The base assembly 12 also includes a cover 62 which has an upper end 64 and a lower end 66 with an outer peripheral surface 68. An opening 70 is formed through the lower end 66 of the cover 62 and the opening 70 extends a distance through the cover 62 generally toward the upper end 64 terminating with an upper, downwardly facing surface 72 formed into the cover 62, the surface 72 being positioned generally near and spaced a distance from the upper end 64 of the cover 62. An upper opening 76 extends through the upper end 64 of the cover 62 and the upper opening 76 extends through the cover 62 intersecting the opening 70, the upper opening 76 having a diameter smaller than the diameter of the opening 70.

A portion of the surface formed by the opening 70 and the cover 62 is threaded generally near the lower end 66 of the cover 62, thereby forming a threaded portion 80. A portion of the outer peripheral surface 38 of the lower base 32 also is threaded generally near the lower end 36, thereby forming a threaded portion 78 on the outer peripheral surface 38 of the lower base 32. The threaded portion 78 is sized and shaped to threadedly engage the threaded portion 80 formed on the outer peripheral surface 68 of the cover 62 in an assembled position of the percutaneous access port 10. Thus, the cover 62 is positioned on the lower base 32 and the threaded portions 78 and 80 cooperate to secure the cover 62 to the lower base 32. In the assembled position of the lower base 32 and the cover 62, the lower end 66 of the cover 62 is generally adjacent the flange 40 on the lower base 32, and the upper end 64 of the cover 62 extends a distance above the upper end 34 of the lower base 32. In this position, the upper end portion of the lower base 32 extends a distance into the opening 70 formed in the cover 62 to a position wherein the upper end 34 of the lower base 32 is spaced a distance from the downwardly facing surface 72 formed in the cover 62.

Two cover access ports 82 and 84 are formed through the upper end 64 of the cover 62, each cover access port 82 and 84 extending through the upper end 64 and through the downwardly facing surface 72 and thereby intersecting the opening 70 in the cover access 62. The cover access port 82 preferably is positioned one hundred and eighty degrees from the cover access port 84, as shown in FIG. 2.

The base assembly 12 also includes a cap 86 which preferably is circularly shaped. The cap 86 is positioned generally adjacent the upper end 64 of the cover 62 and the cap 86 is secured to the upper end 64 of the cover 62 by two screws 88 and 90, as shown in FIG. 2. Two cap access ports 92 and 94 are formed through the cap 86 and the cap access port 92 is positioned one hundred and eighty degrees from the cap access port 94.

In the assembled position, the cap 86 is positioned on the upper end 64 of the cover 62 in a position wherein the cap access port 92 is aligned with the cover access port 82 and the cap access port 94 is aligned with the cover access port 84. The cap access ports 92 and 94 cooperate with the cover access ports 82 and 84 to provide the access ports 16 and 18 in the base assembly 12 and the access port 16 and 18 each are in communication with the opening 70 and cover 62. A cable opening 96 is formed through a central portion of the cap 86, for reasons to be made more apparent below.

The cap 86, more particularly, includes a first cap member 98 and a second cap member 100. The first and the second cap members 98 and 100 are preferably identical in construction.

The cap member 98 includes a semi-circularly shaped portion 102 which is actually larger than a half-circle shape of the entire cap 86. The circularly shaped portion 102 terminates in a flat edge 104. A recess 106 is formed in the flat edge 104 and the recess 106 extends a distance into the first cap member 98 thereby forming a ledge 108.

The cap member 100 includes a semi-circularly shaped portion 110 which is actually larger than a half-circle shape of the entire cap 86. The circularly shaped portion 110 terminates in a flat edge 112. A recess 114 is formed in the flat edge 112 and the recess 114 extends a distance into the first cap member 100 forming a ledge 116.

A cable opening portion 118 is formed in the edge 104 of the first cap member 98 and a cable opening portion 120 is formed in the edge 112 of the second cap member 100. The cable opening portions 118 and 120 each are sized and shaped to provide the cable opening 96 in the assembled position of the first and the second cap members 98 and 100.

In the assembled position of the cap 86, the first cap member 98 is positioned on the second cap member 100 so that the ledge 108 of the first cap member 98 is disposed in the recess 114 of the second cap member 100. The first and the second cap members 98 and 100 are positioned so that the cable opening portion 118 is generally aligned with the cable opening portion 120 and the cable opening portions 118 and 120 cooperate and combine to form the cable opening 96 and the cap 86. When a cable is extending through the cable opening 96, the cap members can be disassembled from such cable portion or assembled on such cable portion by merely removing the first and the second cap members from such cable portion or disposing the first and the second cap members about such cable portion.

The percutaneous access port 10 also includes a plunger 124. The plunger 124 comprises a generally circularly shaped plate 126, having an upper surface 127 and a lower surface 129, and a stem 128. One end of the stem 128 is secured to a central portion of the plate 126 and the stem 128 extends a distance from the plate 126 terminating with an engaging end 130 a plurality of ports 132 are formed through the plate 126, the port 132 being circumferentially spaced about the stem 128 and only two ports 132 being shown in FIG. 1. Additionally, a port is formed through the stem 128 for the same purpose as the ports 132 with the stem 128 being tapered so the seal member 54 does not seal such port.

In an assembled position, the transducer assembly 22 is disposed in the upper opening 76 of the cover 62 and the transducer assembly 22 is sealing connected to the cover 62 in this assembled position thereby closing the upper opening 76. One end of the transducer cable 134 is connected to the transducer assembly 22 in the cover 62 and the transducer cable 134 extends from the transducer assembly 22 upwardly through the cable opening 96 in the cap 86 The septum assembly 20 is disposed on the upper end 64 of the cover 62 and the cap 86 is disposed on the septum assembly 20, the cap 86 being secured to the upper end of the cover 62 by way of the screws 88 and 90 with the septum assembly 20 sealingly disposed between the cap 86 and the upper end 64 of the cover 62. The septum assembly 20 also is disposed between the cap access ports 92 and 94 and the aligned cover access ports 82 and 84 so the septum assembly 20 sealingly closes the access ports 16 and 18, the septum assembly 20 being adapted to provide resealable access through the access ports 16 and 18 to the fluid chamber 14, as mentioned before.

An O-ring seal member 136 is disposed on the upper end 34 of the lower base 32, and the plate 126 of the plunger 124 is disposed on the seal member 136 with the stem 128 of the plunger extending through a central portion of the seal member 136 and through the opening 42 in the upper end 34 of the lower base 32. An O-ring seal member 138 is disposed on the upper surface 127 of the plate 126. Then, the cover 62 with the cap 86 connected thereto is threaded onto the lower base 32 to a position wherein seal member 138 engages the plate 126 of the plunger 124 and forces the plunger 124 in a downward position thereby forcing the stem 128 further through the upper opening 76 to a position wherein the engaging end 130 of the plunger 124 engages the seal member 54 and pushes the seal member 54 downwardly and out of sealing engagement with the sealing surface 44 in the lower base 32. In this position, the cover 62 is threadedly connected to the lower base 32, the stem 128 of the plunger 124 has moved the seal member 54 out of sealing engagement with the sealing surface 44 in the lower base 32 thereby opening the opening 42 through the lower base 32, the seal member 136 forms a seal between the upper end 34 portion of the lower base 32 and the plate 126 and the cover 62, and the seal member 138 forms a seal between the upper surface of the plate 126 of the plunger 124 and the downwardly facing surface 72 formed in the cover 62. In this assembled position, the opening 42 in the lower base 32, the opening in the seal member 136 generally between the plate 126 of the plunger 124 and the upper end 34 of the lower base 32 and the opening in the seal member 138 generally between the plate 126 and the downwardly facing surface 72 in the cover 62 forms the fluid chamber 14. The seal member 138 prevents the plunger 124 from damaging the transducer assembly 22.

In the assembled position of the percutaneous access port 10, the percutaneous access port 10 is implanted in an animal so that the lower end portion 28 of the base assembly 12 extends below the upper surface of the skin 24 of the animal and the upper end 26 portion of the base assembly 12 extends above the upper skin 24 of the animal. In this assembled position, the access ports 16 and 18 thus are accessible from outside the body of the animal and thus access is provided to the fluid of chamber 14 outside the body of the animal. In addition, the transducer cable 134 also extends from outside the body of the animal.

Preferably, a connector 140 is connected to the inlet port 30 formed in the lower end 36 portion of the lower base 32 and the connector 140 is adapted to be connected to tubing (shown in dashed lines in FIG. 1 and designated by the reference numeral 142), the tubing 142 extending from the inlet port 30 in the lower base 32 to the selected organ in the animal and the tubing 142 being operatively connected to the selected organ in the animal in the implanted condition of the percutaneous access port 10. In this position, communication is established between the fluid chamber 14 in the percutaneous access port 10 and the selected organ in the animal by way of the tubing 142, the inlet port 30, the opening 42 and the lower base 32 and in general, the open space between the upper end 34 of the lower base 32 and the downwardly facing surface 72 of the cover 62 or, in other words, between the upper end 34, the lower base 32 and an upper end 64 portion of the cover 62, the fluid chamber 14 also being in communication with the transducer assembly 22 in the assembled an implanted condition of the percutaneous access port 10.

When the percutaneous access port 10 is being utilized to monitor blood pressure in a vessel or artery, the connector 140 is connected either directly to the vessel or artery or one end of the tubing 142 is connected to the connector 140 in the opposite end of the tubing 142 is connected to the selected vessel or artery, the last mentioned made being preferred. Blood flow in the vessel or artery then is inputted through the inlet port 30 into the opening 42 and the lower base 40, through the opening 42 in the lower base 32 and into the open space generally between the upper end 34 of the lower base 32 and the downwardly facing surface 72 on the cover 62, such blood in the fluid chamber 14 also being in communication with the transducer assembly 22. Thus, in this assembled and implanted condition of the percutaneous access port 10, the transducer assembly 22 is in communication with the blood in the connected vessel or artery and the transducer assembly 22 provides a continuous output signal indicative of the pressure of the blood in the fluid chamber 14 of the percutaneous access port 10. In addition, the access ports 16 and 18 provide resealable access to the fluid chamber 14 by way of the septum assembly 20 for injecting substances into the fluid chamber 14 or for injecting flushing substances into the fluid chamber 14 for cleaning purposes.

In one preferred embodiment, the transducer assembly 22 is a commercially available transducer such as available from Konigsberg Instruments, Inc. of Pasadena, Calif., Kongisberg Model No. P5 and the end of the transducer cable 134 opposite the end of the transducer cable 134 which is connected to the transducer assembly 22, is connected through a temperature compensation circuit to a recorder (not shown) for recording the monitored pressures. The septum assembly 20 may be any one of the numerous septum commercially available which provide resealable access such as commercially available from Supelco, Inc. of Bellefonte, Pa. and referred to by Supelco as a Thermogreen Septa LB-2. The lower base 32, the disc 46, the cover 62 and the cap 86 each are constructed of a biocompatible plastic material. The plunger 124 preferably is constructed of a stainless steel and the seal member 54 preferably is constructed of a stainless steel with the spring 52 being constructed of a silicone rubber biocompatible material. The connector 140 is a common connector for connecting tubing to the vessel or to an organ or to a cavity in the body and with this type of connector which is commonly used in the art the tubing is pressure fitted onto the connector 140.

EMBODIMENT OF FIG. 3

Shown in FIG. 3 is a modified percutaneous access port 10a which is constructed exactly like the percutaneous access port 10, except the percutaneous access port 10a does not include a transducer assembly such as the transducer assembly 22 described before with respect to the percutaneous access port 10. Thus, the percutaneous access port 10a will operate in a manner exactly like that described before with respect to the percutaneous access port 10, except the percutaneous access port 10a does not have a transducer assembly for providing output signals indicative of the pressure of the fluid in the fluid chamber 14.

Figure 4:
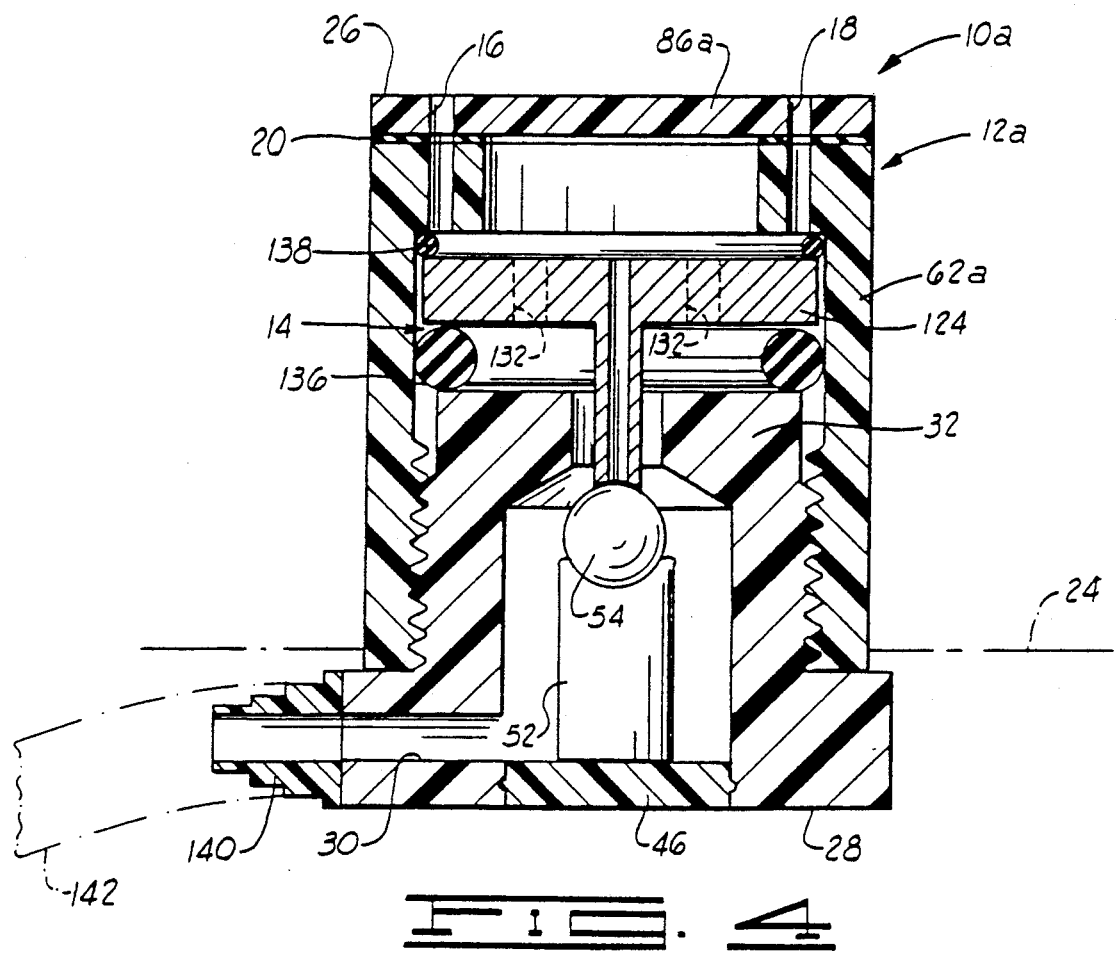
FIG. 4 is a sectional view of a modified percutaneous access port which is constructed in accordance with the present invention.

One advantage of the percutaneous access port 10 and 10a of the present invention is that the percutaneous access port 10 can be implanted in an animal in a manner described before and can be readily modified without removing the entire percutaneous access port 10 from the animal to modify such port to the percutaneous access port 10a. To accomplish this, the cover 62 is unthreaded from the lower base 32 of the percutaneous access port 10 while in an implanted condition of the percutaneous access port 10. As the cover 62 is unthreaded from the lower base 32, the plunger 124 is moved upwardly by the spring 52 and seal member 54 and the seal member 54 is moved into sealing engagement with the sealing surface 44 of the lower base 32. Thus, when the cover 62 has been removed from the percutaneous access port 10, the seal member 54 sealing engages against the sealing surface 44 in the lower base 32 to sealingly close the opening 42 in the lower base 32. This prevents fluid from passing through the inlet port 30 and through the opening 42 in the lower base 32 after the cover 62 has been removed from the lower base 32. After the cover 62 has been removed from the lower base 32, then modified cover 62a is threaded onto the lower base 32 to provide the modified percutaneous access port 10a shown in FIG. 4 and this can be accomplished without removing the percutaneous access port 10 or 10a of the present invention from the implanted condition in the animal.

The access ports 16 and 18 provide easy access to the fluid chamber 14 of either the percutaneous access port 10 or 10a for flushing, administering drugs or withdrawing samples from the fluid chamber 14. In a research situation wherein numerous animals are monitored, one cover 62 with the transducer assembly 22 can be utilized to monitor a number of animals by simply attaching this one cover to the implanted lower base 32 to form the percutaneous access port 10 while the remaining lower bases have modified cover 62a attached thereto to form the percutaneous access port 10a. In addition, even with the cover 62 and transducer assembly 22 connected to form the percutaneous access port 10, the access ports 16 and 18 still are available for flushing, with drawing samples and administering drugs in the manners described before.

The tubing which is connected to the selected organ may be a MICRORENATHANE® type of tubing available from Braintree Scientic, Inc. of Braintree, Mass. This particular type of catheter tubing remains flexible and can be heated in oil to draw its shape out to fit a small tip or flange so it will remain within the body cavity.

In preferred embodiment, a pump (not shown) also can be connected to the tubing or catheter and implanted into the animal. This pump is adapted to pump a heparin solution into the fluid chamber 14 for continuously flushing the fluid chamber 14. In normal operation, an implanted catheter has a life of about twelve days before clotting begins. Using this pump for continuously flushing the system including the catheter, with heparinized saline, this life expectancy can be increased substantially thereby further reducing technician handling time. One pump which would be suitable for use in connection with the percutaneous access port 10 of the present invention in the manner just described is available from Alzet Corporation of Palo Alto, Calif. and referred to as the Alzet ® osmotic pump.

Changes may be made in the construction and operation of the various elements, parts and assembly described herein and changes may be made in the steps or the sequence of steps of the methods described herein without departing from the spirit and scope of the invention as defined in the following claims.

What is claimed is:

1. A method for monitoring blood pressure in a human or an animal, comprising the steps of:

implanting in the human or animal a portion of a percutaneous access port, wherein said portion of the percutaneous access port is implanted into a selected body organ in the human or animal, comprising:

a base assembly having an upper end, a lower end, and an outer peripheral surface;

a fluid chamber formed within a portion of the base assembly;

a transducer disposed within a portion of the upper end of the base assembly in fluidic communication with the fluid chamber;

an inlet port formed in a portion of the lower end of the base assembly in communication with the fluid chamber and connectable to the selected body organ;

wherein the inlet port and at least a portion of the lower end of the base assembly is percutaneously implanted in the selected body organ of the human or animal;

connecting the selected body organ of the human or animal capable of indicating blood pressure having fluid flowing therethrough to the inlet port of the percutaneous access port so that fluid contained in the selected body organ is in communication with the fluid chamber in the percutaneous access port, the transducer sensing pressure of the fluid in the fluid chamber of the percutaneous access port wherein the fluid is from the selected body organ and outputting signals indicative of the pressure of the fluid in the fluid chamber of the percutaneous access port;

wherein the fluid chamber and the transducer are not disposed in the selected body organ of the human or animal; and measuring the blood pressure from the transducer which senses the pressure of the fluid in the fluid chamber of the percutaneous access port.

2. The method of claim 1 wherein the selected body organ comprises a portion of the cardiovascular system.

* * * * *

UNITED STATES PATENT AND TRADEMARK OFFICE
CERTIFICATE OF CORRECTION

PATENT NO. : 5,120,313

DATED : June 9, 1992

INVENTOR(S) : Nancy W. Elftman

It is certified that error appears in the above-identified patent and that said Letters Patent is hereby corrected as shown below:

On the title page, in the title [54], after the word FOR, delete the word "MEASUING" and insert the word --MEASURING--; after the word BLOOD, please delete the word "PRESURE" and insert the word --PRESSURE--; after the word A, please delete the word "PERCUTUANEOUS" and insert the word --PERCUTANEOUS--.

On the title page, the Application No. [21], please delete "749,755", and insert --497,755--.

On the title page, in the Abstract [57], Line 7, please delete the word "gnerally" and insert the word --generally--.

Col. 1, line 2, please delete the word "MEASUING", and insert the word --MEASURING; after the word BLOOD, delete the word "PRESURE", and insert the word --PRESSURE--.

Col. 1, line 2, after the word A, please insert the following, --PERCUTANEOUS ACCESS PORT--.

UNITED STATES PATENT AND TRADEMARK OFFICE
CERTIFICATE OF CORRECTION

PATENT NO. : 5,120,313

DATED : June 9, 1992

INVENTOR(S) : Nancy W. Elftman

It is certified that error appears in the above-indentified patent and that said Letters Patent is hereby corrected as shown below:

Col. 7, line 15, after the word assembled, delete the word "an" and insert the word --and--.

Signed and Sealed this

Second Day of November, 1993

BRUCE LEHMAN

Attest:

Attesting Officer

Commissioner of Patents and Trademarks